United States Patent [19]

Mähl et al.

[11] Patent Number: 5,824,537
[45] Date of Patent: Oct. 20, 1998

[54] PROCESSES FOR THE IN VITRO CULTURE, ATTENUATION OF THE VIRULENCE AND CLONING OF PARASITES OF THE GENUS BABESIA AND THEIR APPLICATIONS

[75] Inventors: Philippe Mähl, Villeneuve-Loubet; Marie-Hélène Dick-Madelpuech, Paris, both of France

[73] Assignee: Laboratoires Virbac, Carros, France

[21] Appl. No.: 525,080

[22] Filed: Sep. 8, 1995

[30] Foreign Application Priority Data

Sep. 8, 1994 [FR] France .................................. 94 10762

[51] Int. Cl.⁶ .............................. C12N 1/00; C12N 1/10; A01N 63/00; A61K 39/018

[52] U.S. Cl. .............................. 435/243; 435/4; 435/7.1; 435/7.22; 435/2.21; 435/34; 435/41; 435/245; 435/258.1; 435/257.4; 435/255.7; 435/70.13; 435/240.1; 424/93.7; 424/270.1

[58] Field of Search .............................. 435/7.22, 34, 41, 435/243, 245, 258.1, 252.4, 253.6, 255.7, 7.21, 7.2, 70.3, 240.1, 4, 7.1; 424/93.7, 270.1

[56] References Cited

U.S. PATENT DOCUMENTS 4,590,072  5/1986  Buening et al. .
4,777,036  10/1988  Laurent .

FOREIGN PATENT DOCUMENTS 018579  11/1980  European Pat. Off. .
220988  5/1987  European Pat. Off. .
382012  7/1990  European Pat. Off. .
2608926  12/1987  France .
2655853  6/1991  France .
2062463  5/1981  United Kingdom .
WO 84/01716  5/1984  WIPO .
WO 91/08771  6/1991  WIPO .
WO 93/14204  7/1993  WIPO .

OTHER PUBLICATIONS

*International Parasitology*, vol. 23, No. 6, Sep. 1993, pp. 771–776.

*Veterinary Parasitology*, vol. 31, No. 3, Jun. 1989, pp. 243–251.

*Chemical Abstracts*, WO 91/11776, 1991.

*Chemical Abstracts*, EP 417,524, 1995.

Davis et al. (1984) J. Clin. Invest. vol. 74, 269–278.

*Primary Examiner*—Paula K. Hutzell
*Assistant Examiner*—Khalid Masoud
*Attorney, Agent, or Firm*—Oblon, Spivak, McClelland, Maier & Neustadt, P.C.

[57] ABSTRACT

The present invention provides a process for the in vitro culture of parasites of the genus Babesia, processes for the in vitro attenuation of the virulence of these parasites, processes for the in vitro cloning of these parasites, attenuated parasites, clonal lines of the genus Babesia, nucleotide probes derived from the clonal lines, the use of these probes for the identification of Babesia parasites and to vaccinces against babesioses.

27 Claims, 6 Drawing Sheets

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 606 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 1:

```
AAGTGATACC TGCCACTGCA TCCTTACACG ATAGACTAGC ATTATGATCC CAGCACATGT      60
TGCAGCACGT ATACGAAACA TATACGTCGT AATGTGACGC CAGATTCACA TGTAGCATGG     120
GCATCATCCC GATCGCCACG CTGGCGTCAG GCCTGGTGCC TCATCACAAT CACGTTCGGA     180
TTATCATGAT ATATTCAATA CATTCATGAT ATAGGCATCA TTCTGACCAC AATATGCGTC     240
CTGTAACGGA TAGGATGCTG TATCTGATGT GGTTCCACTA CATGTTACCT GCCCCGCTTA     300
GGCCCATACC CAGGTGACCT GAGGTCACGA CCACGTGAGC CAAATTTGGC CATCCAGGAT     360
GCAAGTTAGA TTATCGCAGA AAAGAGTCAT CAAGCTCATA TAAAGCGTGT TGGCGCCATT     420
CTAAGCGTAG TTACGCTTGG CTGCGCTGGG CTGTACCACA GGTAACAAAT CCTGAATCAC     480
AGTATCAAGC TGTTGCTTAA AGTCACTTCC TCCATTATTC TGATTAGCCA CACCATCAAT     540
ATCCTTTAAT TCGGTCTTAA GTCCATCCAC CACCTTGGTC TTCCCCTTAC CACTGGTGTT     600
CCACAA                                                                606
```

PROCESSES FOR THE IN VITRO CULTURE, ATTENUATION OF THE VIRULENCE AND CLONING OF PARASITES OF THE GENUS BABESIA AND THEIR APPLICATIONS

BACKGROUND OF THE INVENTION

1. Field of the Invention

The present invention relates to a process for the in vitro culture of parasites of the genus Babesia, to a process for the in vitro attenuation of the virulence of these parasites, to a process for the in vitro cloning of these same parasites, to parasites of attenuated virulence and to clonal lines of the genus Babesia, to nucleotide probes derived from the DNA from these clonal lines, to the use of these probes for the identification of Babesia parasites, to attenuated live vaccines against babesioses and to the applications of the abovementioned processes.

2. Discussion of the Background

Babesioses, also called piroplasmoses, are intraerythrocytic parasitoses, transmitted by tick bites, which affect many domestic and wild animal species and whose agent is a protozoan of the genus Babesia.

There are thus:

a bovine babesiosis caused by *Babesia bovis*, *Babesia bigemina*, *Babesia major* and *Babesia divergens* which is responsible for huge economic losses and represents a major obstacle to increasing the productivity of cattle breeding, especially in developing countries;

a canine babesiosis due to *Babesia canis* and *Babesia gibsoni* and which, each year, kills many dogs or leaves serious sequellae in a number of them;

an equine babesiosis due to *Babesia equi* and *Babesia caballi*;

an ovine babesiosis due to *Babesia ovis*;

a rodent babesiosis caused by *Babesia microti*;

a human babesiosis which is rare but severe since it results in death in more than half of the subjects. The Babesia species implicated in man are usually *Babesia divergens* and *Babesia microti*.

The preparation of vaccines against babesioses has, for these reasons, been the subject of many research studies during the past 20 years.

Several teams have worked toward the extraction and purification of the antigenic principles for their use for the manufacture of vaccines. Thus, there have been proposed:

in EP-A-18 579, a process for the in vitro propagation of Babesia aimed at obtaining, in the culture medium, a soluble antigen, specific for these parasites and capable of being used for immune or diagnostic purposes. This process uses a multiplication of Babesia in erythrocytes placed in a medium comprising 30 to 50% defibrinated serum and maintained in an atmosphere enriched in $CO_2$ (3 to 6%) and with a controlled amount of $O_2$ in order to maintain the hemoglobin of the erythrocytes in the deoxidized state.

This process has proved to be poorly adapted to the multiplication of certain species of Babesia, such as for example *Babesia canis*.

in GB-A-2,062,463, a method consisting in disintegrating, by ultrasound, erythrocytes infested with Babesia and in extracting the specific antigen from the soluble fraction of the suspension thus obtained.

in EP-A-220 988, a process for the in vitro incubation of the *Babesia canis* parasites using erythrocytes infested in an appropriate medium and allowing the specific antigens to be recovered from the supernatant. This culture is performed in a normal atmosphere, that is to say composed essentially of oxygen and nitrogen and lacking a high content of carbon dioxide. It uses two incubations, the first of about 8 hours at a temperature of 34°–38° C., the second of about 16 hours at a temperature of between 0° and 10° C.

Although this process constitutes a definite advance over previous techniques, it has the disadvantage of requiring, in order to initiate the culture, a blood which is very rich in parasites and, consequently, of experimentally infesting splenectomized dogs. In addition, the rate of multiplication of the parasites under these culture conditions remains low, hardly exceeding the coefficient of survival of the parasites. This difficulty is moreover reported in International Application WO 91/08771 in the name of the same patentee which emphasizes that, in cultures of *Babesia divergens* and *Babesia canis*, the parasitemia drops to less than 1% after 3 weeks, such that it is necessary to initiate new cultures and, as a result, to infest splenectomized animals again.

in FR-A-2,608,926, a method for the extraction of an antigen of about 48,000 daltons, specific for *Babesia divergens*, from highly infested ox blood, for use for the preparation of vaccines.

More recently, a number of researchers have looked toward the production of recombinant proteins by identification and cloning of DNA sequences encoding the antigens specific for Babesia and transformation of appropriate host cells such as *Escherichia coli*. These methods are described for example in Applications EP-A-382 012 and EP-A-417 524 or in International Application WO 91/11776.

Attractive from the theoretical point of view but relatively expensive, they appear to be difficult to exploit industrially for the large scale production of vaccines and none of them has been successful.

In addition, immunization with antigenic principles is often found to be incomplete, especially toward heterologous strains and sometimes even toward homologous strains, as shown for example by the vaccination tests described in EP-A-382 012.

SUMMARY OF THE INVENTION

The Applicant consequently set itself the objective of providing a process which makes it possible to attenuate in vitro the virulence of parasites of the genus Babesia so that these parasites can be used for the manufacture of attenuated live vaccines and which is applicable to the different species of Babesia.

The Applicant also set itself the objective of providing a process for the in vitro culture of parasites of the genus Babesia which makes it possible, in a simple and inexpensive manner, to produce these parasites on a large scale for the preparation of vaccines against babesioses and which does not necessitate at any time resorting to a splenectomy in animals.

The Applicant also set itself the objective of providing an attenuated live vaccine, capable of conferring a specific protection against a species of Babesia and regardless of the infestation by the said species (homologous or heterologous strains), without transforming the vaccinated subjects into reservoirs of pathogenic agents and whose production constraints are compatible with industrial exploitation.

The subject of the present invention is a process for the in vitro culture of parasites of the genus Babesia comprising at least one incubation of erythrocytes parasitized by the said parasites in the presence of nonparasitized homologous erythrocytes in a suitable culture medium and under appropriate conditions, characterized in that the said incubation(s) are performed in the presence of cells capable of serving as support for the culture of the said parasites.

DETAILED DESCRIPTION OF PREFERRED EMBODIMENTS

The Applicant has indeed discovered that the in vitro culture of Babesia parasites by incubation of erythrocytes parasitized in the presence of non-parasitized erythrocytes in an appropriate culture medium makes it possible to obtain a very productive growth of these parasites when this culture is performed in the presence of cells capable of serving as support for the said culture of the parasites, for example, by the formation of a bottom layer.

In a preferred embodiment of the process in accordance with the invention, the said cells are animal cells derived from immortal lines such as, for example, the C32 cells (human melanoma cells), the MDCK cells (dog kidney cells), the BHK21 cells (newborn hamster kidney cells) or the AK-D cells (cat fetal pulmonary cells).

By way of examples, the C32, MDCK and AK-D cells are available from the AMERICAN TYPE CULTURE COLLECTION where they are identified under references CRL 1585, CCL 34 and CCL 150 respectively.

However, the Applicant has been able to verify that other animal cells such as for example monocytes or lymphocytes make it possible to carry out the culture process in accordance with the invention.

The incubation of the erythrocytes is performed in the presence of a sufficient quantity of the said cells so as to allow the growth of the parasites, these cells being preferably nonconfluent.

According to an advantageous arrangement of the process in accordance with the invention, the culture medium is a liquid medium of the RPMI 1640, MEM, M199 or WILLIAMS type and the like, supplemented with 2 to 40% of decomplementized homologous or heterologous serum and/or of a serum substitute and, optionally, growth factors such as hypoxanthine, antibiotics such as gentamycin, penicillin, streptomycin, antifungal agents or anti-oxidants, the said culture medium being in addition buffered so as to maintain the pH between 7 and 7.7.

The culture of the parasites can, however, also be performed in a semiliquid medium.

In accordance with the present invention, the ratio between the volume of the erythrocytes present in the culture and the volume of the culture medium is between 0.1 and 50%, advantageously between 2.5 and 10% and, preferably, equal to 5%.

The incubation of the erythrocytes is performed at a temperature of between 30° between [sic] 40° C. and, preferably, close to 37° C.

In accordance with the invention, the culture process comprises, for the continuous culture of the parasites, several successive incubations.

It is, indeed, possible to perform a continuous culture of the parasites according to the principle of subcultures, that is to say by the incubation, in new culture wells, of a dilution of the parasitized erythrocytes recovered at the end of a previous incubation, the said dilution corresponding to the addition of the parasitized erythrocytes to nonparasitized erythrocytes in order to reduce the parasitemia.

According to a particularly advantageous arrangement of the process in accordance with the invention, the first incubation may be performed with parasitized erythrocytes or zoites obtained from blood of animals infected with Babesia.

In accordance with the present invention, the culture process comprises, in addition, the preservation at low temperature of the parasitized erythrocytes in a medium comprising a cryopreserving agent such as for example dimethyl sulfoxide and a macromolecule with a high osmotic power such as, for example, polyvinylpyrrolidone.

It is possible to culture, by the culture process in accordance with the invention, the different species of Babesia, and especially *Babesia canis, Babesia gibsoni, Babesia bovis, Babesia bigemina, Babesia major, Babesia divergens, Babesia equi, Babesia caballi, Babesia ovis* and *Babesia microti*.

The culture process in accordance with the invention finds application in the mass production of parasites of the genus Babesia.

It also finds application in the detection of an asymptomatic Babesia infection.

The subject of the present invention is also a process for the in vitro attenuation of the virulence of parasites of the genus Babesia, characterized in that it comprises the culture of the said parasites according to the in vitro culture process in accordance with the invention for at least 8 days.

The Applicant has, indeed, discovered that by culturing Babesia parasites according to the culture process in accordance with the invention for a sufficient period, an attenuation or even a disappearance of the virulence of the said parasites is obtained.

In a preferred embodiment of the attenuation process in accordance with the invention, the culture of the parasites is performed for a period of between 20 and 60 days.

The attenuation of the virulence of the parasites can be checked by injecting the parasites of the ongoing culture into a sensitive animal.

This process makes it possible to attenuate the virulence of parasites of different species of Babesia, and especially of *Babesia canis, Babesia gibsoni, Babesia bovis, Babesia bigemina, Babesia major, Babesia divergens, Babesia equi, Babesia caballi, Babesia ovis* and of *Babesia microti*.

The attenuation process in accordance with the invention finds application especially in the preparation of attenuated live vaccines.

The subject of the present invention is also parasites of the genus Babesia of attenuated virulence other than those belonging to the species *Babesia bovis, Babesia bigemina* and *Babesia divergens*.

In a preferred embodiment of the invention, the parasites of attenuated virulence belong to the species *Babesia canis*.

The subject of the present invention is also a process for the in vitro cloning of parasites of the genus Babesia, comprising:

a) the isolation of a single parasite from a suspension of erythrocytes parasitized with the said parasites or from a population of zoites,
  b) the culture of the isolated parasite by the in vitro culture process in accordance with the invention, stages a) and b) being carried out once or several times until a homogeneous line of parasites is obtained.

In accordance with the invention, the isolation of the parasite may be performed by a limiting dilution of the suspension of parasitized erythrocytes or of the population of zoites or by means of a cell sorter or alternatively by micromanipulation.

Limiting dilution is understood to mean, for the purpose of the present invention, a sufficiently high dilution of the suspension of parasitized erythrocytes or of the population of zoites used such that, in all probability, only 0 or 1 parasitized erythrocyte or zoite is introduced into each culture well and that, as a result, a homogeneous line derived from a single parasite develops in each well.

Macromanipulation is understood to mean the aspiration into a micropipette of a single parasitized erythrocyte under visual control.

It is possible to obtain, by the process in accordance with the invention, clonal lines of numerous Babesia species, and especially of Babesia canis, Babesia gibsoni, Babesia bovis, Babesia bigemina, Babesia major, Babesia divergens, Babesia egui, Babesia caballi, Babesia ovis and of Babesia microti.

The cloning process in accordance with the invention finds application especially in the preparation of attenuated live vaccines.

The subject of the present invention is also a clonal line of parasites of the genus Babesia other than those belonging to the species Babesia bovis, Babesia bigemina and Babesia divergens.

In a preferred embodiment of the invention, the clonal line is a line of parasites belonging to the species Babesia canis.

According to an advantageous arrangement of this embodiment, the clonal line is the line designated hereinafter as PIII of Babesia canis, deposited at the EUROPEAN COLLECTION OF ANIMAL CELL CULTURES on the date of 6 Sep. 1994 and identified in this Collection under No. 94090611.

The subject of the present invention is also an oligonucleotide probe, characterized in that it is derived from the DNA of parasites of the PIII clonal line.

Advantageously, the oligonucleotide probe has all or part of the following sequence:

babesiosis caused by Babesia canis and consists of erythrocytes parasitized by the PIII clonal line of Babesia canis.

The subject of the invention is also an attenuated live vaccine against a babesiosis, characterized in that it consists of erythrocytes parasitized by parasites of the genus Babesia obtained by any one of the processes described above.

Such a vaccine can indeed be prepared:
  either with parasitized erythrocytes derived from the culture of a strain of parasites which are naturally avirulent or not very virulent which are used according to the culture process in accordance with the invention;
  or with parasitized erythrocytes derived from the culture of a strain which naturally has a virulence which is more or less pronounced but whose virulence will have been previously attenuated by the attenuation process in accordance with the invention;
  or, finally, from the culture of a clonal line obtained by the cloning process in accordance with the invention and having an extremely weak virulence.

BRIEF DESCRIPTION OF THE DRAWINGS

The invention will be understood more clearly with the aid of the following description which is made by way of example and with reference to the accompanying drawings in which.

```
5'
AAGTGATACC  TGCCACTGCA  TCCTTACACG  ATAGACTAGC  ATTATGATCC   50
CAGCACATGT  TGCAGCACGT  ATACGAAACA  TATACGTCGT  AATGTGACGC  100
CAGATTCACA  TGTAGCATGG  GCATCATCCC  GATCGCCACG  CTGGCGTCAG  150
GCCTGGTGCC  TCATCACAAT  CACGTTCGGA  TTATCATGAT  ATATTCAATA  200
CATTCATGAT  ATAGGCATCA  TTCTGACCAC  AATATGCGTC  CTGTAACGGA  250
TAGGATGCTG  TATCTGATGT  GGTTCCACTA  CATGTTACCT  GCCCCGCTTA  300
GGCCCATACC  CAGGTGACCT  GAGGTCACGA  CCACGTGAGC  CAAATTTGGC  350
CATCCAGGAT  GCAAGTTAGA  TTATCGCAGA  AAAGAGTCAT  CAAGCTCATA  400
TAAAGCGTGT  TGGCGCCATT  CTAAGCGTAG  TTACGCTTGG  CTGCGCTGGG  450
CTGTACCACA  GGTAACAAAT  CCTGAATCAC  AGTATCAAGC  TGTTGCTTAA  500
AGTCACTTCC  TCCATTATTC  TGATTAGCCA  CACCATCAAT  ATCCTTTAAT  550
TCGGTCTTAA  GTCCATCCAC  CACCTTGGTC  TTCCCCTTAC  CACTGGTGTT  600
CCACAA                                                     606
3'
```

The subject of the present invention is, moreover, the use of this oligonucleotide probe to identify parasites of the genus Babesia.

According to an advantageous arrangement, this oligonucleotide probe makes it possible, in addition, to differentiate the strains and/or clonal lines of parasites of the genus Babesia.

The subject of the present invention is also an attenuated live vaccine against a babesiosis, characterized in that it comprises erythrocytes parasitized by parasites of the genus Babesia other than those belonging to the species Babesia bovis, in a pharmacologically acceptable vehicle.

Figure 4:
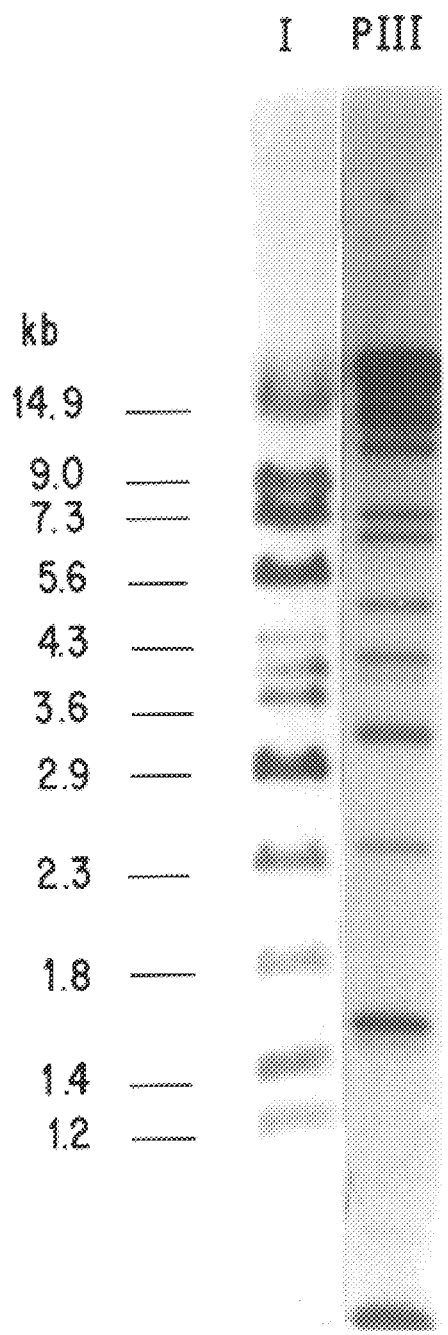
Figure 5:
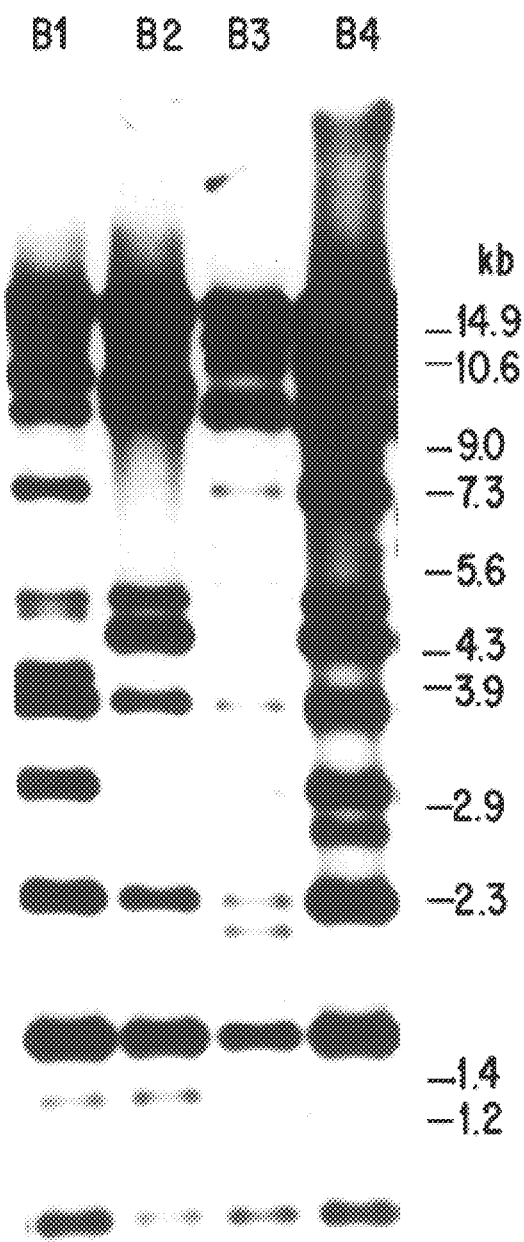

In a preferred embodiment of the invention, the vaccine is capable of inducing an effective protection against canine tively with a vaccine prepared from the PIII clonal line and with a prior art vaccine, after administration of a virulent strain of Babesia canis;

FIG. 4 represents the profile of the restriction fragments which is obtained after a double digestion with the restriction enzymes AseI/BamHI, from the genomic DNA of the PIII clonal line of Babesia canis;

FIG. 5 represents the profiles of the restriction fragments, which are obtained after a double digestion with the restriction enzymes AseI/BamHI, from strains of Babesia canis derived from dogs suffering from a babesiosis.

Figure 6:
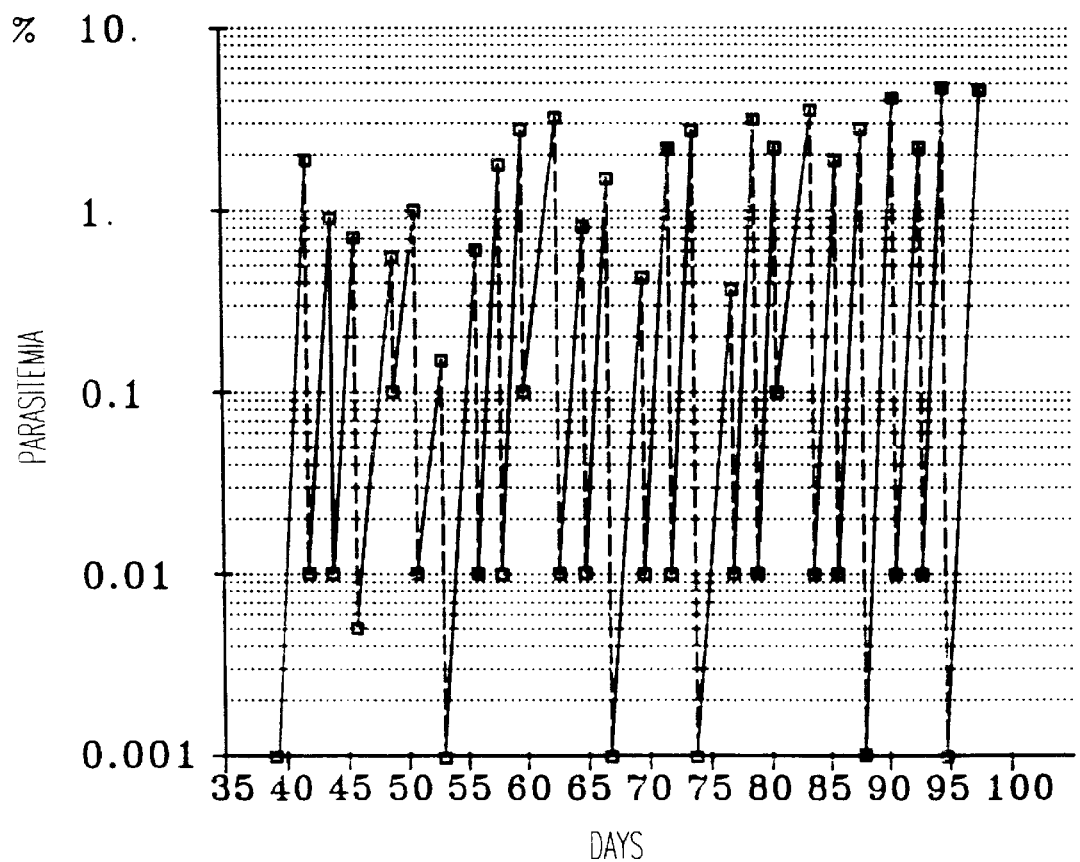

FIG. 6 represents the growth of Babesia canis parasites which is obtained by a variant of the in vitro culture process in accordance with the invention.

EXAMPLE 1

CULTURE OF THE CELLS INTENDED TO SERVE AS SUPPORT FOR THE CULTURE OF THE PARASITES

The present Example uses AK-D cells capable of multiplying in a culture medium which is appropriate and suitable for use as bottom layers in the culture of Babesia parasites.

1) Origin of the AK-D Cells

The AK-D cells are obtained from the strain deposited at the AMERICAN TYPE CULTURE COLLECTION under number CCL 150.

These cells are preserved by freezing according to the following procedure:

after counting in a counting chamber, the cells are centrifuged at 1200 g for 5 minutes. The supernatant is removed. Freezing medium (RPMI 1640/FCS/DMSO - v/v: 75/15/10) is added to the cell pellet in an appropriate volume in order to obtain a cell concentration equal to $2\times10^6$ cells/ml. The cell suspension thus obtained is divided into 1 ml samples which are preserved in liquid nitrogen.

2) Medium for Culturing the AK-D Cells

The AK-D cells are cultured in a liquid culture medium having the composition below:

| | |
|---|---|
| fetal calf serum | 5 ml |
| glutamine | 2 mM |
| gentamycin | 2.5 mg |
| supplemented RPMI 1640 medium | qs 50 ml |

This medium is filtered on a 0.22 µm membrane.

For the purposes of the present invention, supplemented RPMI 1640 medium is understood to mean a liquid medium having the composition below:

| | |
|---|---|
| RPMI 1640 powder | 10.4 g |
| HEPES | 8.3 g |
| NaHCO$_3$ | 2 g |
| hypoxanthine | 0.001 g |
| water | qs 1 liter |

This medium is filtered on a 0.22 µm membrane.

3) Preparation of Cellular Bottom Layers from Frozen AK-D Cells

A 1 ml sample containing $2\times10^6$ frozen AK-D cells is rapidly thawed at 37° C. The cells are suspended in a tube containing 10 ml of the culture medium described above. The tube is subjected to centrifugation at 400 g for 10 minutes. The supernatant is removed and their pellet is taken up in 5 ml of culture medium in a 25 cm$^2$ cell culture bottle. The cells are allowed to grow until they become confluent, that is to say about 3 days.

When the cells are confluent, the supernatant is discarded and the cells are rapidly washed twice with 5 ml of supplemented RPMI medium. 2 ml of a 0.25% trypsin-EDTA solution are added. The separation of the cells is monitored under a microscope. When the cells are separated from each other, the cell suspension is taken up in culture medium, centrifuged at 400 g for 10 minutes and the pellet obtained is taken up in 5 ml of culture medium. It is then possible to count the AK-D cells in a counting chamber with the aid of a drop of cell suspension.

This cell suspension may be maintained by successive subculturings in 25 cm$^2$ cell culture bottles at a rate of 5 ml of culture medium per bottle and of $2\times10^5$ cells/ml of culture medium. During each subculturing, the cells are allowed to grow until they become confluent, that is to say about 3 days. They are then subjected to a treatment with a 0.25% trypsin-EDTA solution as described above, at the end of which they can be counted and diluted in order to obtain a new suspension having $2\times10^5$ cells/ml, which can be used for a new subculturing.

The use of freshly thawed AK-D cells to serve as bottom layers in a culture of Bahesia parasites requires that the culture of AK-D cells is previously subjected to three subculturings as described above. At the end of the third subculturing, the AK-D cells can be inoculated into the wells of a cell culture plate.

To do this, 1 ml of cell suspension containing $3\times10^4$ AK-D cells is deposited in each well of a 24-well plate. The inoculation of Babesia can be performed on these cells from the next day.

EXAMPLE 2

CULTURE OF *BABESIA CANIS* PARASITES

The in vitro culture of the *Babesia canis* parasites according to the process in accordance with the invention can be initiated by means of parasitized erythrocytes or of *Babesia canis* zoites obtained from infected dog blood, which were freshly collected or preserved at room temperature or by freezing.

The present example uses parasitized erythrocytes obtained from blood samples collected from dogs having a symptomatic piroplasmosis caused by *Babesia canis* and which had been preserved by freezing.

1) Treatment of the Blood Samples and Preservation of the Parasitized Erythrocytes After centrifugation of the blood samples at 1200 g for 10 minutes, the volume of globular pellets obtained is measured. The supernatants are removed and the pellets are mixed with a freezing medium (v/v : 1/1) having the following composition:

| | |
|---|---|
| DMSO (dimethyl sulfoxide) | 40 g |
| polyvinylpyrrolidone 40 (SIGMA) | 20 g |
| supplemented RPMI 1640 | qs 100 ml | and having been previously filtered on a 0.45 µm membrane.

The mixture of erythrocytes-freezing medium is stored in liquid nitrogen.

The DMSO may be advantageously replaced by another cryopreserving agent such as, for example, glycerol. The polyvinylpyrrolidone, a macromolecule with a high osmotic power, may be replaced by other high molecular weight compounds also having a high osmotic power.

2) Preparation of the Fresh Nonparasitized Erythrocytes

The nonparasitized erythrocytes used for the culture of the *Babesia canis* parasites are isolated from blood samples collected from dogs of the Beagle breed of group A$^-$, raised under S.P.F (specific pathogen free) conditions and free of any Babesia infection.

The blood samples are subjected to a centrifugation at 2200 g for 10 minutes. The plasma and the white blood cells are removed. The erythrocytes are washed twice with 10 volumes of supplemented RPMI 1640. At the end of the second washing, the globular pellet is taken up in a volume of supplemented RPMI 1640 sufficient to obtain a suspension of fresh nonparasitized erythrocytes having a hematocrit of 50%.

3) Initiation of the *Babesia canis* Culture Starting with Frozen Parasitized Erythrocytes A vial containing 200 μl of a frozen mixture of parasitized erythrocytes and of supplemented RPMI 1640 is left to thaw in a water bath at 37° C. for 1 minute.

1 ml of a 3.5% NaCl solution is added to the vial and the whole is subjected to a centrifugation at 400 g for 5 minutes.

Figure 1A:
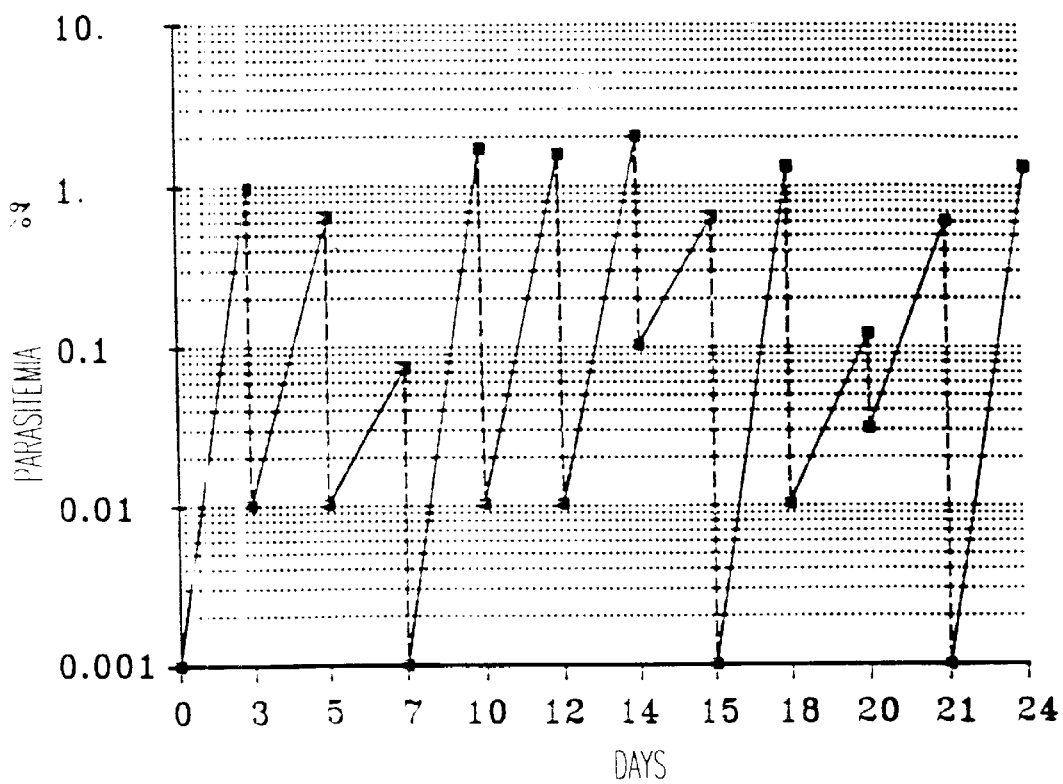
FIGS. 1A and 1B show the growth of Babesia canis parasites obtained respectively by the in vitro culture process in accordance with the invention and by a prior art culture process.

The supernatant is removed and the pellet is taken up in 1 ml of a liquid culture medium having the composition below:

| | |
|---|---|
| dog serum | 0.05 ml |
| Nutridoma ® SR | 0.02 ml |
| glutamine | 2 mM |
| gentamycin | 50 μg |
| supplemented RPMI 1640 | qs 1 ml |
| pH = 7.3 | |

The dog serum entering into the composition of the medium for culturing the parasites is available from the company EUROBIO. Before being added to the other constituents of this culture medium, it is decomplemented at 56° C. for 30 minutes, and then filtered through a 0.5 μm membrane.

Nutridoma® SR is a serum substitute which is available from the company BOEHRINGER MANNHEIM.

A suspension of parasitized erythrocytes capable of being used to initiate an in vitro culture of *Babesia canis* is thus obtained.

The initiation of this culture is achieved according to the following procedure:

on D0, the *Babesia canis* parasites are inoculated into the wells of a 24-well culture plate previously inoculated with AK-D cells by removing the AK-D cell culture medium present in the wells and by depositing into each well 1 ml of the suspension of parasitized erythrocytes prepared above as well as 50 μl of a suspension of fresh nonparasitized erythrocytes prepared as described at point 2) above. The 24-well plate is then placed in a candle incubation chamber or in an incubator with regulation of $O_2$ and $CO_2$, under an atmosphere enriched in $CO_2$ (3 to 7%) and low in $O_2$ (5 to 17%). The candle chamber is itself placed in an oven at 37° C.

In the middle of the day, the culture medium, that is to say the liquid covering the sedimented erythrocytes, is removed and replaced with an identical volume of fresh culture medium.

the next day (D1) and the day after that (D2), the culture medium is replaced with an identical volume of fresh culture medium. 25 μl of suspension of fresh nonparasitized erythrocytes may be added into each well.

on D3, a smear is done:

if the smear does not make it possible to reveal the presence of parasites, the cultures are diluted ½ according to the procedure described below:

removal of the culture medium from the culture which should be subjected to dilution, taking up of the erythrocytes of this culture with the aid of 200 μl of fresh culture medium, depositing half the volume thus obtained in a culture well, addition of 0.9 ml of fresh liquid culture medium and of 50 μl of suspension of fresh nonparasitized erythrocytes.

This dilution has the effect of supplying the culture both with fresh nonparasitized erythrocytes and with fresh culture medium.

if this smear reveals a percentage of parasitized erythrocytes greater than or equal to 0.2%, the parasite cultures are subjected to a dilution suitable for inoculating the wells of a new culture plate with a suspension of erythrocytes parasitized at 0.01% and for performing a continuous culture of the parasites under the conditions indicated at point 4) below.

on D5, another smear is done on the cultures whose smear was negative on D3:

if the smear does not reveal the presence of parasites, the culture medium is changed without dilution.

if the smear makes it possible to reveal a percentage of parasitized erythrocytes greater than or equal to 0.2%, the cultures are subjected to a dilution suitable for allowing the inoculation of the wells of a new culture plate with a suspension of erythrocytes parasitized at 0.01% and for performing a continuous culture of the parasites.

on D6, a new smear is done on the cultures whose smear was negative on D5. Depending on the result of this smear, dilutions are made as on D3.

This procedure is continued up to D10 and, in the case where no parasitemia is then detectable, it is advisable to initiate a new culture from another vial of parasitized erythrocytes.

In all cases, each *Babesia canis* culture should be transferred every 2 days onto a new bottom layer of AK-D cells.

4) Conditions for the Continuous Culture of the *Babesia canis* Parasites

The in vitro continuous culture of the *Babesia canis* parasites is performed according to the principle of subcultures, each subculture consisting in incubating, in new culture wells, a dilution of parasitized erythrocytes collected at the end of a previous incubation.

For subcultures performed in 24-well plates, the conditions below proved particularly advantageous:

deposition of the parasitized erythrocytes into culture wells containing a bottom layer of AK-D cells, initial parasitemia of the subcultures: 0.01%, hematocrit of the subcultures: about 5%, that is to say a supply of 100 μl of a suspension of fresh nonparasitized erythrocytes and of about 0.9 ml of liquid culture medium, pH of the culture medium: 7.3, incubation in a candle incubation chamber or in an incubator with regulation of $O_2$ and $CO_2$, under an atmosphere enriched in $CO_2$ (3 to 7%) and low in $O_2$ (5 to 17%) and at a temperature of 37° C.

Under these conditions, the percentage of parasitized erythrocytes present in the culture medium is at least equal to 1% and may reach values 10 times greater after 48 hours of incubation.

The incubation is stopped. The erythrocytes and the culture medium are recovered and are subjected to a dilution suitable for allowing the inoculation of new culture wells with a suspension of erythrocytes parasitized at 0.01% and the incubation of these erythrocytes.

5) Preservation of the Parasitized Erythrocytes Collected at the End of an Incubation The parasitized erythrocytes collected at the end of an incubation can be either used to maintain the culture of the said parasites by subcultures under the conditions specified above, or can be frozen as described in point 1) of Example 2 and preserved in liquid nitrogen.

6) Growth of the *Babesia canis* Parasites During a Continuous Culture

FIG. 1A shows the parasitic growth obtained during a continuous culture of *Babesia canis* parasites in accordance with the invention.

The variation of the parasitemia represented in FIG. 1A was established by initiating a *Babesia canis* culture with a percentage of parasitized erythrocytes equal to 0.001% and by carrying out subcultures with a parasitemia either of 0.001% (D7, D15, D21), or of 0.01% (D3, D5, D10, D12, D18), or of 0.03% (D20), or alternatively of 0.1% (D14). The dotted lines correspond to the dilutions of the parasitized erythrocytes in non-parasitized erythrocytes capable of decreasing the parasitemia. The culture conditions were moreover in accordance with those described above.

This FIG. 1A shows that not only does the culture process in accordance with the invention make it possible to obtain from very low (<0.1%) percentages of parasitized erythrocytes, a high parasitic growth, but also that it is capable of allowing maintenance of this growth during a continuous culture.

Figure 1B:
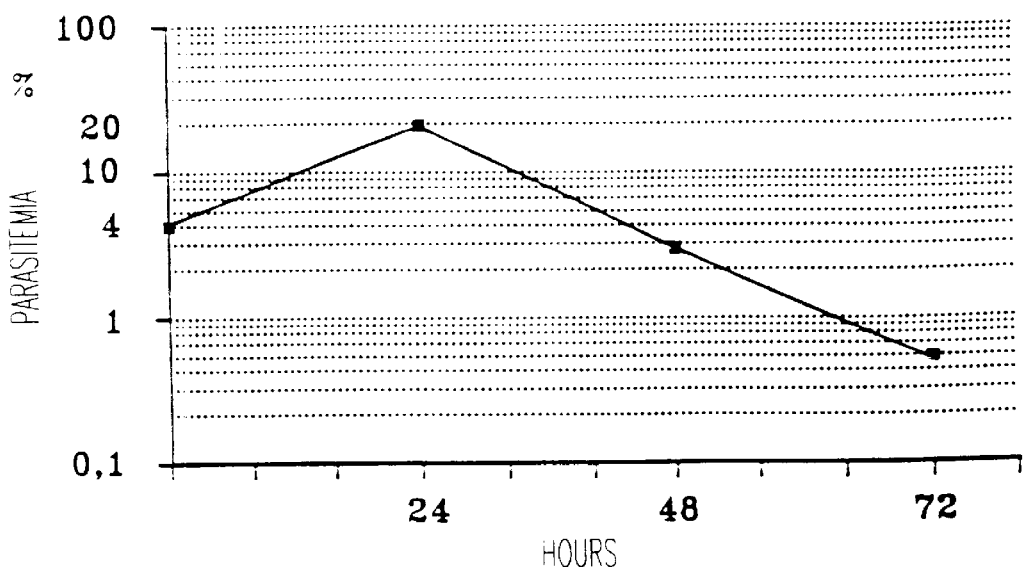

By way of comparison, FIG. 1B shows the growth of *Babesia canis* parasites obtained during an in vitro culture performed according to the procedure described by MOREAU and SOULA (Bull. Soc. Sci. Vét. et Méd. comparée, 1979, 81, no. 5). A *Babesia canis* culture initiated with a percentage of parasitized erythrocytes of 4% makes it possible to obtain an increase in the level of erythrocytes parasitized during the first 24 hours (up to 20%) but the latter drops from the 24th hour and reaches a value below the initial parasitemia at around the 48th hour.

EXAMPLE 3

ATTENUATION OF THE VIRULENCE OF A STRAIN OF *BABESIA CANIS*

A virulent strain of *Babesia canis* whose inoculation via the intravenous route into dogs causes the appearance of signs of massive infestation and death within eight days was cultured for 40 days under the culture conditions described in Example 2.

At the end of the culture, the attenuation of the virulence of this strain was tested by inoculation, also via the intravenous route, into sensitive dogs.

Figure 2A:
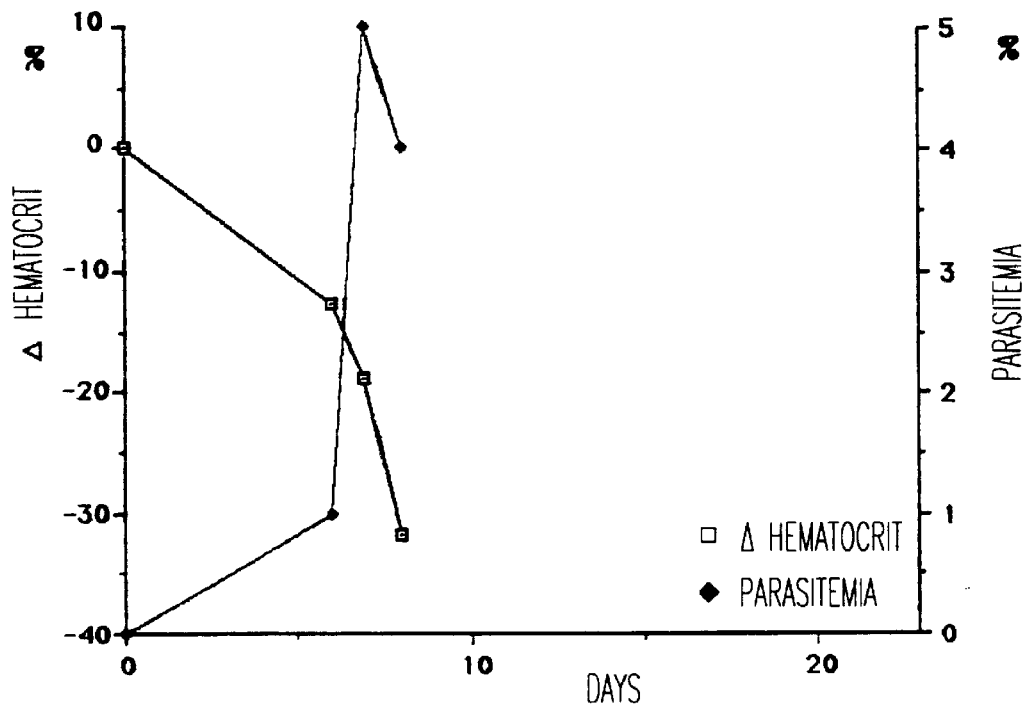
FIGS. 2A and 2B show the variation of the hematocrit and of the parasitemia in dogs inoculated respectively with a virulent strain of Babesia canis and the same strain after attenuation by the attenuation process in accordance with the invention.
Figure 2B:
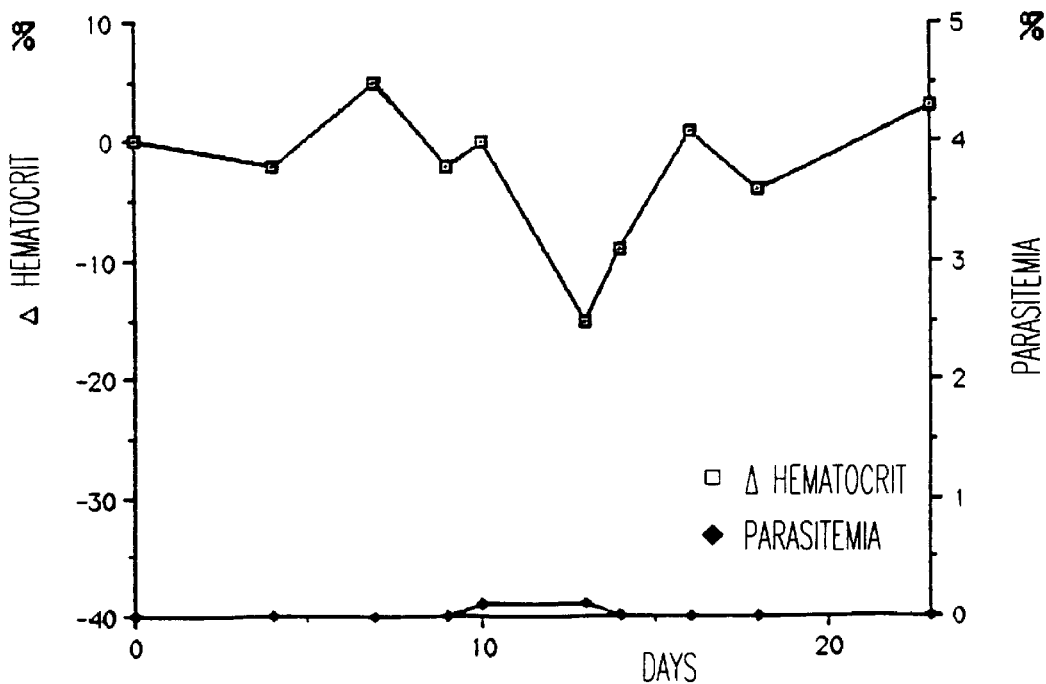

FIGS. 2A and 2B show the variation of the value of the hematocrit and of the intravenous parasitemia exhibited by the dogs having received the strain before it is cultured and this same strain after a 40-day culture, respectively.

As shown in FIG. 2A, the inoculation of the strain before culture (Day 0 on the x-axis) results in a fall in the hematocrit and the appearance of parasitemia which reaches a level of 10% within a few days. These biological signs are accompanied by clinical signs such as anorexia, adynamia, hyperthermia, hematuria and neurological disorders which result in the death of the dogs by the 8th day in the absence of a curative treatment.

When the same strain is inoculated into sensitive dogs after having been previously cultured for 40 days according to the culture process in accordance with the invention, the dogs have, as visible in FIG. 2B, a discrete decrease in the hematocrit which is accompanied by the appearance of a very low intravenous parasitemia. The latter disappears spontaneously within a few days whereas the hematocrit value undergoes a correction. The dogs do not exhibit, furthermore, any clinical sign of a Babesia infection.

EXAMPLE 4

PRODUCTION AND SELECTION OF A CLONAL LINE OF *BABESIA CANIS*

1) Production of a Clonal Line

The cloning of *Babesia canis* parasites can be performed using parasitized erythrocytes obtained from a continuous culture as described in point 4) of Example 2.

To do this, the erythrocytes and the liquid culture medium collected at the end of a culture are subjected to a centrifugation at 1000 g for 10 minutes at room temperature. The supernatant is removed and the parasitemia of the pellets is determined.

The pellet is then subjected to a new centrifugation at 1500 g for 3 minutes at room temperature. The supernatant is removed and the pellet is resuspended.

With the aid of a counting chamber, the number of erythrocytes present in one $\mu$l is determined and the number of erythrocytes parasitized per $\mu$l of pellet is calculated.

The latter is diluted in a volume of liquid culture medium so as to obtain one parasitized erythrocyte in 300 $\mu$l of suspension.

100 $\mu$l of the said suspension are deposited into each well of a 96-well culture plate containing a lawn of AK-D cells so as to deposit one parasitized erythrocyte every 3 wells and the hematocrit of the culture is adjusted to 2.5% by adding to the wells an appropriate volume of a suspension of fresh nonparasitized erythrocytes.

The 96-well plate is left to incubate, as described above, in a candle incubation chamber under an atmosphere enriched in $CO_2$ and low in $O_2$ and at a temperature of 37° C.

On D2, 100 $\mu$l of liquid culture medium are added to each well. The hematocrit is adjusted to 5% by the addition of an appropriate volume of suspension of fresh nonparasitized erythrocytes and the culture plate is replaced in an incubation chamber.

Every two days, from D4 to D12, the appearance of parasites in each well is checked by a smear:

the cultures whose parasitemia is negative are subjected to a ½ dilution, transferred onto new bottom layers of AK-D cells and replaced in an incubation chamber.

the cultures whose parasitemia is positive can then be subjected to a continuous culture capable of producing an amplification of the clone thus obtained, under the conditions described in point 4) of Example 2.

Repeated twice, this procedure made it possible to obtain so-called "tertiary" clones of *Babesia canis,* that is to say homogeneous lines of parasites, each derived from a single parasite and whose properties are stable in vitro and in vivo.

The clones may be frozen as described in point 1) of Example 1 and preserved in liquid nitrogen.

2) Selection of a Clonal Line

The selection of a clonal line, for its use for the manufacture of vaccines, uses three criteria:

its avirulence in vivo (absence of specific symptoms of a babesiosis within a period of 10 days after inoculation of the clonal line into a sensitive animal), its rate of growth in culture in vitro, its genetic profile established by the genetic fingerprinting method.

It is on the basis of these criteria that the Applicant selected the PIII clonal line of *Babesia canis*. The latter has been deposited at the EUROPEAN COLLECTION OF ANIMAL CELL CULTURES on the date of 6 Sep. 1994 and identified in this Collection by the number 94090611.

EXAMPLE 5

PREPARATION OF A VACCINE AGAINST CANINE BABESIOSIS

An attenuated live vaccine against canine babesiosis can be prepared with parasitized erythrocytes derived:

either from the culture of a strain of *Babesia canis* parasites which are naturally avirulent or not very virulent;

or from the culture of a strain of *Babesia canis* naturally having a virulence which is more or less pronounced but whose virulence will have been previously attenuated;

or, finally, from the culture of a clonal line of *Babesia canis* such as, for example, the PIII clonal line, having an extremely weak virulence.

The vaccinal doses are prepared from frozen parasitized erythrocytes which are diluted in a pharmacologically acceptable vehicle such as, for example, NaCl at 3.5%.

The vaccine may be administered into dogs subcutaneously, intramuscularly or intravenously. The primary vaccination comprises two injections at 3 week intervals and must be supplemented by an annual booster.

EXAMPLE 6

IMMUNIZATION WITH A VACCINE IN ACCORDANCE WITH THE INVENTION

1) Vaccine Prepared from an Attenuated Strain

The efficacy of a vaccine prepared from an attenuated strain was demonstrated by the administration, to previously vaccinated dogs, of virulent strains collected from dogs suffering from babesiosis and originating from different French departments.

The virulent strains inoculated and their geographical origin are specified in Table 1 below:

TABLE 1

| ORIGIN | STRAINS |
|---|---|
| GIRONDE | Bo*, SG* |
| LANDES | MA*, MB*, MD* |
| LOT-et-GARONNE | VLA |
| HAUTE GARONNE | VB |
| PYRENEES ATLANTIQUES | NA*, NR, NS, NT |
| HAUTES-PYRENEES | GA |
| BAS-RHIN | G2, G4, G6, G8, G10, G12 |

The strains accompanied by an asterisk are extremely virulent, causing the death of the infested dogs.

Table 2 below presents the results of this study:

TABLE 2

| STRAINS INOCULATED | VACCINAL EFFICACY |
|---|---|
| Bo* | + |
| G2 + G4 + G6 | + |
| G8 + G10 + G12 | + |
| VLA + VB + GA | + |
| NR + NS + NT | + |
| SG* + MB* + NA* | + |
| MD* + MA* | + |

2) Vaccine Prepared from the PIII Clonal Line

The efficacy of this vaccine was demonstrated by the intravenous administration of a particularly virulent strain of *Babesia canis* (strain originating from Bordeaux) to dogs having received, intravenously, 21 days before this administration, a vaccinal dose prepared from the PIII clonal line.

The immunization was assessed by the monitoring of three criteria: the appearance of an intravenous parasitemia, the variation of the hematocrit value and the general condition of the dogs.

Figure 3A:
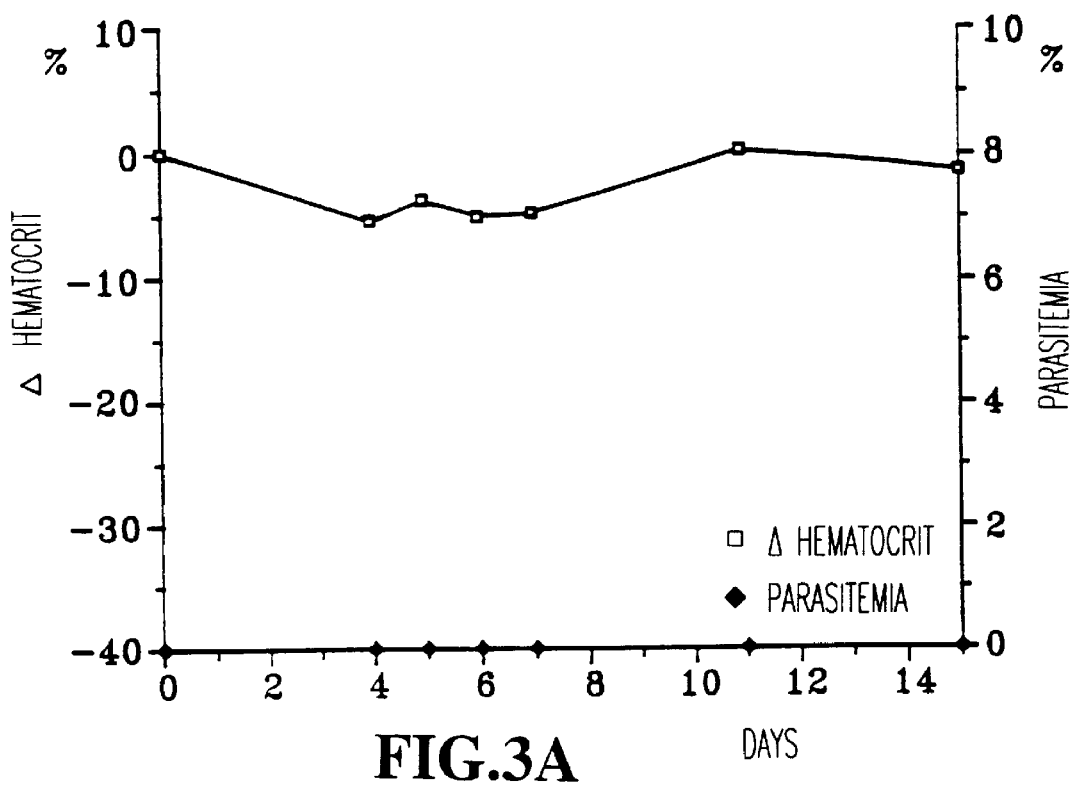
FIGS. 3A and 3B show the variation of the hematocrit and of the parasitemia in dogs, previously vaccinated respec-

As visible in FIG. 3A, the intravenous parasitemia of the dogs remains zero during the fourteen days following the administration of the virulent strain (Day 0 on the x-axis) and the hematocrit value does not undergo significant variations during the same period. In addition, the dogs manifest no symptom of a *Babesia canis* infection.

Figure 3B:
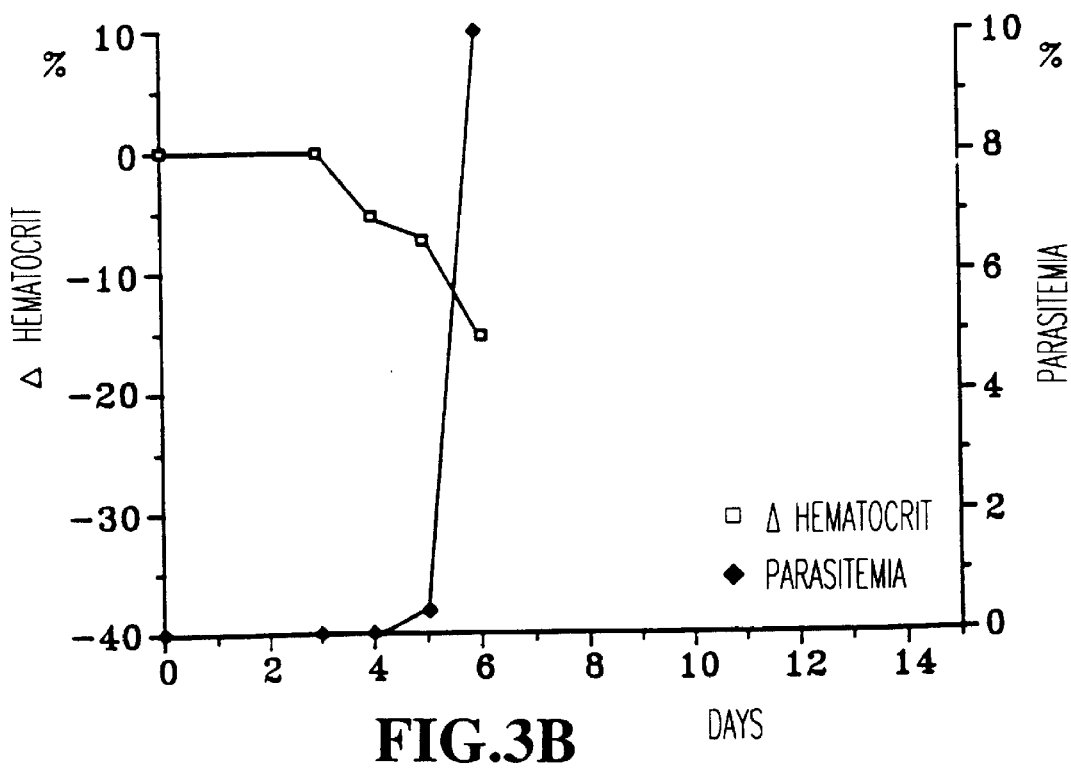

By way of comparison, FIG. 3B shows the immunization obtained, under the same conditions and against the same virulent strain, with the aid of an inactivated vaccine of the prior art marketed under the name PIRODOG® by the company RHONE MERIEUX. The dogs were vaccinated via the subcutaneous route in accordance with the vaccination procedure recommended by the manufacturer.

Following the administration of the virulent strain (Day 0 on the x-axis), a drop in the hematocrit was observed from the 3rd day and a sharp rise in the dogs' intravenous parasitemia was observed from the 4th day, clinically accompanied by nervous signs and by hematuria and resulting in the death of the dogs by the 6th day.

In addition, the efficacy of this attenuated vaccine was tested against a large number of strains collected from dogs infected with Babesia and living in various French regions.

These strains and their geographical origin are presented in Table 3 below.

TABLE 3

| GIRONDE | LANDES | LOT-ET-GARONNE | PYRENEES ATLANTIQUES | PARIS |
|---|---|---|---|---|
| Bo | MA | VLA | FB | P |
| SA | MB | VLB | FC | |
| SAC | MC | VLC | NA | BASRHIN |
| SAD | MD | VLG | NB | G1 |
| SAE | ME | VLH | NC | G2 |
| SAF | MF | VLI | NE | G3 |
| SAG | MI | VLJ | NF | G4 |
| SAH | MJ | VLK | NG | G5 |
| SAL | MK | VLL | NH | G6 |
| SAM | ML | VLM | NN | G8 |
| SAJ | MN | VLN | NO | G10 |
| SAK | MO | | NP | G12 |
| SAL | MP | HAUTE GARONNE | NQ | G13 |
| SB | MQ | VA | NR | G14 |
| SC | MR | VB | NS | G15 |
| SE | MS | VD | NT | G16 |
| SG | VE | | | G17 |
| SH | | | | G18 |
| GIRONDE | | | HAUTES-PYRENEES | BAHRHIN |
| SJ | | | GA | G19 |
| SK | | | | G20 |
| SL | | | AUDE | G21 |
| SN | | | CA | G22 |
| SQ | | | | G23 |
| SR | | | | G24 |
| SS | | | | G25 |
| ST | | | | G26 |
| SU | | | | G27 |
| SV | | | | G28 |
| SW | | | | G29 |
| SX | | | | G30 |
| SCA | | | | G31 |
| SCB | | | | G32 |
| SCC | | | | G33 |
| SCD | | | | G35 |
| | | | | G36 |
| | | | | G38 |
| | | | | G39 |
| | | | | G40 |

These tests made it possible to show that the administration of a vaccine prepared from the PIII clonal line confers protection against 100% of the French strains tested.

EXAMPLE 7

PRODUCTION OF AN OLIGONUCLEOTIDE PROBE FROM THE DNA OF THE PIII CLONAL LINE AND MOLECULAR CHARACTERIZATION OF THIS LINE

The recent molecular biological techniques allow a very fine genetic identification based on polymorphism of the DNA in certain sequences, especially sequences repeated several times in the genome (and often of repetitive nature).

In *Plasmodium falciparum,* another intraerythrocytic parasite and an agent for malaria, several of these sequences have been isolated and have made it possible to demonstrate a polymorphism of the restriction patterns which makes it possible to differentiate parasitic clones from each other (GOMAN et al., Mol. Biochem. Parasitol., 1982, 5, 391–400).

It is a similar approach which the Applicant followed in order to identify and characterize the PIII clone of *Babesia canis.*

1) Extraction of the DNA of the Parasites of the PIII Clone

Parasitized erythrocytes collected at the end of a culture were subjected, after centrifugation, to lysis with the aid of PBS (0.137 mM NaCl, 10 mM $Na_2HPO_4$, 3.2 mM $KH_2PO_4$, pH 7.4), supplemented with 0.02% saponin, and then subjected to a centrifugation at 400 g.

The parasites collected in the supernatant were washed with PBS and centrifuged at 3000 g in order to remove the hemoglobin and the membranes. The parasites were lysed in a TE buffer comprising 10 mM tris-HCl and 1 mM ethylenediaminetetraacetic acid (EDTA) of pH 8, supplemented with 0.5% SDS. The lysates were incubated overnight in the presence of proteinase K (1 mg/ml) and subjected to two successive extractions with the aid of a phenol-chloroform-isoamyl alcohol mixture (25:24:1), and then to an extraction with the aid of chloroform. The DNA present in the aqueous phase was precipitated by the addition of 3 volumes of ethanol at room temperature and then dried, resuspended in TE buffer, treated with ribonuclease A (100 µg/ml), and then with proteinase K (200 µg/ml).

This suspension was subjected to 3 extractions as above, precipitated, dried and resuspended in TE buffer before being subjected to dialysis in the presence of TE buffer on a cellulose disk of porosity 0.05 µm.

2) Preparation of the Probes

The genomic DNA extracted from parasites of the PIII clone was digested with DNaseI in the presence of $MnCl_2$ (1 to 10 mM) in order to obtain fragments of between 0.5 and 2 kbp. After having provided the DNA fragments with blunt ends, NotI linking segments were added, the DNA was digested with the NotI restriction enzyme, then separated from the digested linking segments and the fragments with sequences of less than or equal to 2 kb on Biogel A50M (PHARMACIA LKD). The linked DNA was inserted into the vector Lambda ZAP II (STRATAGENE) and the recombinant phages obtained were amplified in *Escherichia coli* XL1 Blue strain bacteria.

15000 recombinant phages corresponding to one hundredth of the library were screened by hybridization on nylon membranes with the total DNA of parasites of the PIII clone labeled according to the technique described by FEINBERG and VOGELSTEIN (Analyt. Biochem., 1983, 132, 6) in an amount of $1\times10^9$ cpm per µg with ($\alpha^{32}P$) DATP. The hybridizations were performed overnight at 65° C. in the presence of 6×SSC, a 5× Denhardt solution, 100 µg/ml of denatured salmon sperm and 0.5% SDS. The membranes were then washed twice with 2×SSC supplemented with 0.5% SDS at room temperature for 15 minutes and twice with 0.1×SSC supplemented with 0.5% SDS at 65° C. for 20 minutes and autoradiographed overnight at −70° C.

36 very strongly radiolabeled phages, capable of containing repeat and/or repetitive sequences, were selected. The genomic inserts were located by an excision system in vivo in the plasmid vector pBluescript® II (SHORT et al., Nucleic Acids Res., 1988, 16, 7583–7600) and recovered by digesting the plasmid DNA with the NotI restriction enzyme. After electrophoresis on a 1.2% agarose gel, the inserts were purified using Spin X columns (COSTAR).

4 inserts corresponding to 4 different families were radiolabeled according to the technique described by FEINBERG and VOGELSTEIN and used as probes in Southern blot analyses of the restriction fragment length polymorphisms.

3) Restriction Fragment Length Polymorphism Analysis

Different strains of parasites of diverse geographical origins were cultured by the in vitro culture process in accordance with the invention in order to obtain a sufficient number of parasites to allow the extraction of their DNA.

The extraction of the DNA from the PIII clonal line and from these strains was performed according to the method described in point 1) of the present Example, after lysis of the parasitized erythrocytes.

The DNA concentration was determined by a spectrophotometric measurement and its integrity checked on an agarose gel. The DNAs were subjected to a total digestion by means of one or more restriction enzymes (AseI, AseI/BamHI, EcoRI . . . ) and the products of digestion were separated by electrophoresis on a 0.8% agarose gel before being transferred onto nylon membranes in the presence of 20×SSC.

The membranes were subjected to a hybridization with the abovementioned labeled probes under similar conditions described above, with the exception of the hybridization medium consisting of 50% formamide and 1% SDS.

The final washing was performed with the aid of 0.1×SSC supplemented with 0.5% or 1% of SDS.

4) Results

The hybridization experiments with the 4 probes tested confirmed that the latter are repeated in the genome of the strains, thus validating the hypothesis on which their isolation was based.

One of these probes was retained for the reason that it makes it possible to obtain the most easily interpretable genetic profiles, both as regards the intensity of the signal and the number and the distribution of the DNA fragments obtained by digestion with restriction enzymes such as the combination AseI/BamHI.

This probe has the following sequence:

```
5'
AAGTGATACC  TGCCACTGCA  TCCTTACACG  ATAGACTAGC  ATTATGATCC     50
CAGCACATGT  TGCAGCACGT  ATACGAAACA  TATACGTCGT  AATGTGACGC    100
CAGATTCACA  TGTAGCATGG  GCATCATCCC  GATCGCCACG  CTGGCGTCAG    150
```

-continued

| | | | | | | |
|---|---|---|---|---|---|---|
| GCCTGGTGCC | TCATCACAAT | CACGTTCGGA | TTATCATGAT | ATATTCAATA | | 200 |
| CATTCATGAT | ATAGGCATCA | TTCTGACCAC | AATATGCGTC | CTGTAACGGA | | 250 |
| TAGGATGCTG | TATCTGATGT | GGTTCCACTA | CATGTTACCT | GCCCCGCTTA | | 300 |
| GGCCCATACC | CAGGTGACCT | GAGGTCACGA | CCACGTGAGC | CAAATTTGGC | | 350 |
| CATCCAGGAT | GCAAGTTAGA | TTATCGCAGA | AAAGAGTCAT | CAAGCTCATA | | 400 |
| TAAAGCGTGT | TGGCGCCATT | CTAAGCGTAG | TTACGCTTGG | CTGCGCTGGG | | 450 |
| CTGTACCACA | GGTAACAAAT | CCTGAATCAC | AGTATCAAGC | TGTTGCTTAA | | 500 |
| AGTCACTTCC | TCCATTATTC | TGATTAGCCA | CACCATCAAT | ATCCTTTAAT | | 550 |
| TCGGTCTTAA | GTCCATCCAC | CACCTTGGTC | TTCCCCTTAC | CACTGGTGTT | | 600 |
| CCACAA | | | | | | 606 |
| 3' | | | | | | |

This probe is specific for *Babesia canis* DNA and is sensitive, offering a detection threshold of about 10 to 20 pg, which should correspond in analogy with *Plasmodium falciparum* to 1000 to 2000 parasites.

FIG. 4 shows the genomic profile obtained after a double digestion with the restriction enzymes AseI/BamHI and a hybridization with the probe described above, of DNA from Babesia of the PIII clonal line which are directly derived from an in vitro culture (profile designated PIII) performed under the conditions described in Example 2. The molecular weight marker is denoted by the letter I.

Under the conditions, the genomic DNA of the PIII clonal line comprises 16 restriction fragments of about 17 kb, about 16 kb, about 15 kb, 13 kb, 11.5 kb, 7.1 kb, 6.6 kb, 4.8 kb, 3.8 kb, 3.6 kb, 3.15 kb, 2.3 kb, 1.5 kb, 1.4 kb, 0.9 kb and 0.6 kb respectively.

FIG. 5 shows the genomic profiles obtained after a double digestion with the restriction enzymes AseI/BamHI of the DNA from Babesia of strains collected from dogs suffering from a babesiosis and originating from the same region (profiles designated B1, B2, B3 and B4), and hybridization with the probe described above.

As shown in this FIG. 5, the strains collected from dogs suffering from a babesiosis, although they originate from the same region, have different and specific genomic profiles, thus confirming the discriminating power of the probe selected.

The use of other restriction enzymes would generate other genomic profiles which would be equally specific for the strains of Babesia.

EXAMPLE 8

DETECTION OF AN ASYMPTOMATIC *BABESIA CANIS* INFECTION

It has been shown that dogs are often carriers of an asymptomatic infection caused by *Babesia canis* which is not detectable under a microscope. This has been established in the past by inoculating blood from these dogs into animals which have developed the disease.

The culture process in accordance with the invention has a sensitivity such that it makes it possible to reveal asymptomatic infections at a very low parasitemia.

A study was performed on 43 live clinically healthy dogs in a biotope which is very favorable to *Dermacentor reticulatus,* a tick vector for the parasites *Babesia canis,* and which are therefore highly exposed to the risk of transmission of a canine babesiosis. These dogs had, prior to this study, been the subject of a prophylaxis against ticks (weekly 0.5% dimpylate bath from March to October).

These dogs were subjected to two blood sample collections, within an interval of 2 to 5 months, during the six months following the stopping of the prophylactic treatment.

These samples were subjected, on the one hand, to a direct examination for the presence of a parasitemia by microscopy according to conventional techniques used in parasitology and, on the other hand, to an in vitro culture in accordance with the culture process of the present invention.

1) Search for a Parasitemia by in Vitro Culture

The search for a parasitemia by in vitro culture was performed according to the following procedure: The blood samples were subjected to a centrifugation at 2200 g for 5 minutes, followed by two washes of the pellet obtained with RPMI 1640 supplemented22 [sic] at the same speed of centrifugation. The supernatant was removed.

In the wells of a 24-well plate, the culture medium for freshly subcultured AK-D cells was replaced with 1 ml of Babesia culture medium, 50 µl of the blood pellet to be tested and 50 µl of a suspension of fresh erythrocytes diluted 50% in supplemented RPMI 1640. The culture plates were left to incubate under the same conditions as those described in Example 2.

The appearance of a parasitemia was monitored by doing a smear on the cultures every 48 hours, accompanied by a ½ dilution of the cultures in the case where the smear proved to be negative, and this up to the 10th day.

2) Results

The microscopic examination of the 86 blood samples did not make it possible to detect the presence of *Babesia canis* parasites.

However, 20 cultures out of 86 revealed the presence of parasites, that is to say that 14 dogs out of 43, that is to say a third of the total number, were confirmed at least once as healthy carriers of the parasite.

As shown by this study, the use of the process for the in vitro culture of Babesia makes it possible to detect the carrying of these parasites in animals having no symptom of an infection and in which a direct examination by microscopy does not make it possible to detect a parasitemia.

EXAMPLE 9

CULTURE OF *BABESIA CANIS* PARASITES IN THE PRESENCE OF C32 CELLS

An in vitro culture of Babesia canis parasites was performed in accordance with the invention, using C32 cells (human melanoma cells) obtained from the strain deposited at the AMERICAN TYPE CULTURE COLLECTION under number CRL 1585.

These cells are capable, just like the AK-D cells, of multiplying in an appropriate medium such as that described in point 2) of Example 1 and of constituting cellular bottom layers which can serve as support for the culture of Babesia parasites.

The bottom layers of C32 cells were prepared from frozen cells according to the procedure described in point 3) of Example 1.

The culture of *Babesia canis* parasites was initiated from parasitized erythrocytes as described in point 3) of Example 2, and then continued continuously while performing subcultures with a parasitemia of either 0.001%, or 0.005%, or 0.01% or even 0.1%.

The conditions under which these subcultures were performed (hematocrit, pH, temperature, $O_2$ and $CO_2$ contents, and the like) are identical to those defined in point 4) of Example 2.

FIG. 6 shows the parasitic growth obtained between the 38th day and 97th day, that is to say during a period of 59 days, for a continuous culture of *Babesia canis* parasites performed in the presence of C32 cells under these conditions.

As evident from the above, the invention is not in the least limited to the implementations, embodiments and applications which have just been described more explicitly; on the contrary, it embraces all the variants which may occur to a specialist in this field without departing from the framework or the scope of the present invention.

2. The process of claim 1, wherein the process comprises, after step (a), the additional step of:
   (b) obtaining the parasites.

3. The process of claim 1, wherein the immortal animal cell line is the AK-D cell line having ATCC Accession No. CCL 150.

4. The process of claim 1, wherein the culture medium is selected from the group consisting of RPMI 1640 medium, minimal essential medium (MEM), medium 199 (M199), and Williams medium; wherein the culture medium comprises from 2% to 40% (v/v) of a serum composition selected from the group consisting of a decomplementized homologous serum, a decomplementized heterologous serum, and a serum substitute; and wherein the culture medium has a pH of between 7 and 7.7.

5. The process of claim 1, wherein the culture medium comprises a growth factor.

6. The process of claim 1, wherein the culture medium comprises an antibiotic.

7. The process of claim 1, wherein the culture medium comprises an antifungal agent.

---

---

We claim:

1. A process for the in vitro culture of parasites of the genus Babesia comprising the steps of:
   (a) incubating in a culture medium erythrocytes parasitized by the parasites, wherein the incubation is performed in the presence of nonparasitized homologous erythrocytes and in the presence of an immortalized animal cell line other than erythrocytes or Babesia parasites.

8. The process of claim 1, wherein the culture medium comprises from 0.1% to 50% (v/v) of the erythrocytes.

9. The process of claim 8, wherein the culture medium comprises from 2.5 to 10% (v/v) of erythrocytes.

10. The process of claim 1, wherein the erythrocytes parasitized by the parasites are from the blood of an animal infected with the parasites.

11. The process of claim 1, further comprising, after step (a), the additional step of preserving parasitized erythrocytes in a freezing medium.

12. The process of claim 11, wherein the freezing medium comprises a cryopreserving agent and a macromolecule having a high osmotic power.

13. The process of claim 1, wherein the parasites belong to a species selected from the group consisting of *Babesia canis, Babesia gibsoni, Babesia bovis, Babesia bigemina, Babesia major, Babesia divergens, Babesia equi, Babesia caballi, Babesia ovis,* and *Babesia microti.*

14. A process for the in vitro culture of parasites of the genus Babesia comprising the steps of:
(a) incubating in a culture medium erythrocytes parasitized by the parasites, wherein the incubation is performed in the presence of nonparasitized homologous erythrocytes, and in the presence of an immortalized animal cell line other than erythrocytes or Babesia parasites;
(b) collecting parasitized erythrocytes;
(c) diluting the collected parasitized erythrocytes; and
(d) incubating in a culture medium the diluted parasitized erythrocytes, wherein the incubation is performed in the presence of nonparasitized homologous erythrocytes, and in the presence of an immortalized animal cell line other than erythrocytes or Babesia parasites.

15. The process of 14, wherein, after step (d), steps (b), (c), and (d) are repeated at least once.

16. A process for the in vitro culture of parasites of the genus Babesia comprising the steps of:
(a) isolating a single parasitized erythrocyte from a suspension of erythrocytes parasitized by the parasites; and
(b) incubating in a culture medium the isolated parasitized erythrocyte, wherein the incubation is performed in the presence of nonparasitized homologous erythrocytes, and in the presence of an immortalized animal cell line other than erythrocytes or Babesia parasites.

17. The process of claim 16, wherein, in step (a), the single parasitized erythrocyte is isolated by means of a limiting dilution of the suspension of erythrocytes, by means of a cell sorter, or by means of a micromanipulation.

18. The process of claim 16, wherein the parasites belong to a species selected from the group consisting of *Babesia canis, Babesia gibsoni, Babesia bovis, Babesia bigemina, Babesia major, Babesia divergens, Babesia equi, Babesia caballi, Babesia ovis,* and *Babesia microti.*

19. A process for the in vitro culture of parasites of the genus Babesia comprising the steps of:
(a) isolating a single parasitized erythrocyte from a suspension of erythrocytes parasitized by the parasites;
(b) incubating in a culture medium the isolated parasitized erythrocyte, wherein the incubation is performed in the presence of nonparasitized homologous erythrocytes, and in the presence of an immortalized animal cell line other than erythrocytes or Babesia parasites;
(c) collecting parasitized erythrocytes;
(d) isolating a single parasitized erythrocyte from the collected parasitized erythrocytes; and
(e) incubating in a culture medium the single parasitized erythrocyte isolated in step
(d) wherein the incubation in step (e) is performed in the presence of nonparasitized homologous erythrocytes, and in the presence of an immortalized animal cell line other than erythrocytes or Babesia parasites.

20. The process of 19, wherein, after step (e), steps (c), (d), and (e) are repeated at least once.

21. A process for the in vitro culture of parasites of the genus Babesia comprising the steps of:
(a) incubating in a culture medium a population of zoites of the Babesia, wherein the zoites are from the blood of a first animal infected with the Babesia, wherein the incubation is performed in the presence of nonparasitized erythrocytes from a second animal belonging to the same species as the first animal, and in the presence of an immortalized animal cell line other than erythrocytes or Babesia parasites;
(b) collecting parasitized erythrocytes;
(c) diluting the collected parasitized erythrocytes; and
(d) incubating in a culture medium the diluted parasitized erythrocytes, wherein the incubation is performed in the presence of nonparasitized homologous erythrocytes, and in the presence of an immortalized animal cell line other than erythrocytes or Babesia parasites.

22. The process of 21, wherein, after step (d), steps (b), (c), and (d) are repeated at least once.

23. A process for the in vitro culture of parasites of the genus Babesia comprising the steps of:
(a) isolating a single zoite from a population of zoites of the Babesia, wherein the single zoite is from the blood of a first animal infected with the Babesia; and
(b) incubating in a culture medium the single zoite isolated in step (a), wherein the incubation is performed in the presence of nonparasitized erythrocytes from a second animal belonging to the same species as the first animal, and in the presence of an immortalized animal cell line other than erythrocytes or Babesia parasites.

24. The process of claim 23, wherein, in step (a), the single zoite is isolated by means of a limiting dilution of the population of zoites, by means of a cell sorter, or by means of a micromanipulation.

25. The process of claim 23, wherein the parasites belong to a species selected from the group consisting of *Babesia canis, Babesia gibsoni, Babesia bovis, Babesia bigemina, Babesia major, Babesia divergens, Babesia equi, Babesia caballi, Babesia ovis,* and *Babesia microti.*

26. A process for the in vitro culture of parasites of the genus Babesia comprising the steps of:
(a) isolating a single zoite from a population of zoites of the Babesia, wherein the single zoite is from the blood of a first animal infected with the Babesia,
(b) incubating in a culture medium the single zoite isolated in step (a), wherein the incubation is performed in the presence of nonparasitized erythrocytes from a second animal belonging to the same species as the first animal, and in the presence of an immortalized animal cell line other than erythrocytes or Babesia parasites;
(c) collecting parasitized erythrocytes;
(d) isolating a single parasitized erythrocyte from the collected parasitized erythrocytes; and
(e) incubating in a culture medium the single parasitized erythrocyte isolated in step
(d), wherein incubation is performed in the presence of nonparasitized homologous erythrocytes and in the presence of an immortalized animal cell line other than erythrocytes or Babesia parasites.

27. The process of 26, wherein, after step (e), steps (c), (d), and (e) are repeated at least once.

* * * * *